(12) United States Patent
Nair et al.

(10) Patent No.: US 12,287,308 B2
(45) Date of Patent: Apr. 29, 2025

(54) MELDRUM'S ACID ACTIVATED FURAN (MAF) MASS SPECTROMETRY COMPATIBLE STAINING AGENT FOR PROTEINS IN POLYACRYLAMIDE GELS

(71) Applicant: Amrita Vishwa Vidyapeetham, Tamil Nadu (IN)

(72) Inventors: Sobha Vijayan Nair, Kerala (IN); Ramachandran Nair Prakash Chandran, Kerala (IN); Bipin Nair, Kerala (IN); Sudarslal Sadasivan Nair, Kerala (IN); Kalyani Ajayan, Kerala (IN)

(73) Assignee: Amrita Vishwa Vidyapeetham (IN)

( * ) Notice: Subject to any disclaimer, the term of this patent is extended or adjusted under 35 U.S.C. 154(b) by 784 days.

(21) Appl. No.: 17/570,625

(22) Filed: Jan. 7, 2022

(65) Prior Publication Data

US 2023/0119761 A1   Apr. 20, 2023

(30) Foreign Application Priority Data

Oct. 20, 2021   (IN) .............................. 202141047710

(51) Int. Cl.
*G01N 27/447* (2006.01)
*C07K 1/26* (2006.01)
*G01N 33/68* (2006.01)

(52) U.S. Cl.
CPC ......... *G01N 27/44726* (2013.01); *C07K 1/26* (2013.01); *G01N 33/6803* (2013.01)

(58) Field of Classification Search
CPC . C07K 1/26; G01N 27/44726; G01N 33/6803
See application file for complete search history.

(56) References Cited

U.S. PATENT DOCUMENTS

| | | | |
|---|---|---|---|
| 2006/0021876 A1* | 2/2006 | Ruefer ..................... | C07K 1/26 204/465 |
| 2012/0234678 A1* | 9/2012 | Diller ...................... | C07K 1/26 436/15 |
| 2019/0219591 A1* | 7/2019 | Nair .................... | G01N 33/6842 |

OTHER PUBLICATIONS

Ravindran, Archana. Chromogenic Biomolecules: Analytical Applications. Diss. Amrita Vishwa Vidyapeetham , 2017. (Year: 2017).*
Diaz et al., "A versatile and Highly Selective Colorimetric Sensor for the Detection of Amines", Chemistry—A European Journal, vol. 23, Issue 15, pp. 3562-3565 (2017) (Year: 2017).*

* cited by examiner

*Primary Examiner* — Jennifer Wecker
(74) *Attorney, Agent, or Firm* — Donald R. Boys; Central Coast; Patent Agengy LLC

(57) ABSTRACT

A method for visualizing a macromolecule fragment pattern resulting from gel electrophoresis has steps for preparing a polyacrylamide gel in an electrophoresis apparatus, treating the polyacrylamide gel with Meldrum's acid Activated Furan (MAF) dissolved in a suitable solvent, loading a protein sample to a prepared position in the gel, and resolving the protein sample by applying an electrical potential across the gel for a period of time, separating molecular fragments of the protein into the fragment pattern in the gel. The method is characterized in that the MAF stains the molecular fragments in a manner to be discernible by human vision and by conventional analysis techniques.

12 Claims, 19 Drawing Sheets

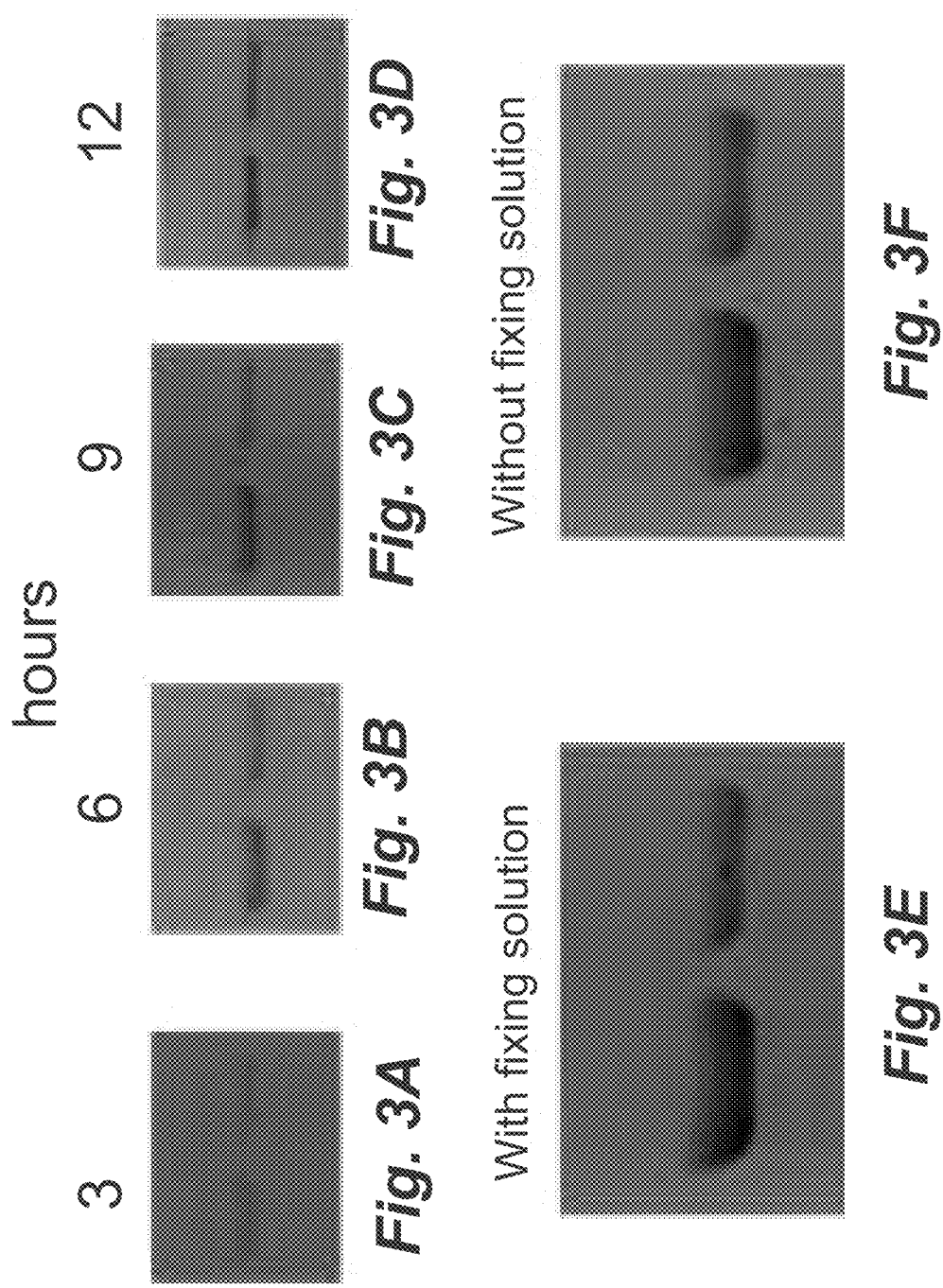

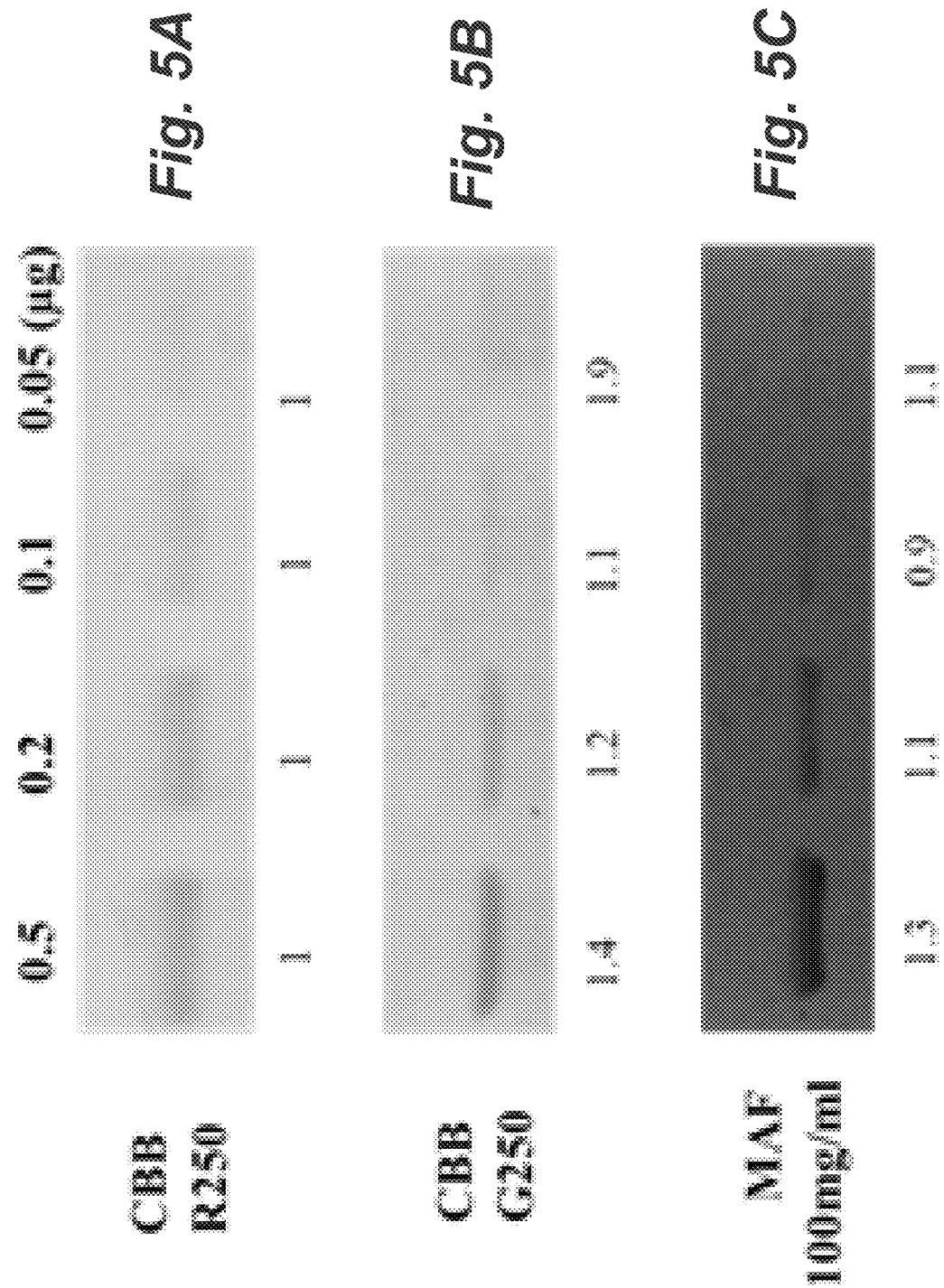

| S.No | Observed m/z | Charge | Observed mass (Da) | Theoretical mass (Da) | ppm | Peptide | Sequence coverage |
|---|---|---|---|---|---|---|---|
| 1 | 461.752 | 2 | 921.489 | 921.481 | 9 | AEFVEGVTK | |
| 2 | 700.354 | 2 | 1398.69 | 1398.69 | 6 | TVMENFVAFVDK | |
| 3 | 740.406 | 2 | 1478.80 | 1478.79 | 7 | LGEYGFQNALIVR | |
| 4 | 523.256 | 3 | 1566.74 | 1566.74 | 6 | DAFLGSFLYEYSR | 15 % |
| 5 | 784.383 | 2 | 1566.75 | 1566.74 | 10 | DAFLGSFLYEYSR | |
| 6 | 547.321 | 3 | 1638.94 | 1638.93 | 7 | KVPQVSTPTLVEVSR | |
| 7 | 575.621 | 3 | 1723.84 | 1723.83 | 7 | MPCTEDYLSLILNR | |
| 8 | 627.648 | 3 | 1879.92 | 1879.91 | 5 | RPCFSALTPDETYVPK | |

Table 1

*Fig. 7A*

| S.No | Observed m/z | Charge | Observed mass (Da) | Theoretical mass (Da) | ppm | Peptide | Sequence coverage |
|---|---|---|---|---|---|---|---|
| 1 | 395.241 | 2 | 788.467 | 788.464 | 4 | LVTDLTK | |
| 2 | 461.748 | 2 | 921.482 | 921.481 | 1 | AEFVEVTK | |
| 3 | 464.253 | 2 | 926.491 | 926.486 | 6 | YLYEIAR | |
| 4 | 507.815 | 2 | 1013.61 | 1013.61 | 2 | QTALVELLK | |
| 5 | 381.578 | 3 | 1141.71 | 1141.71 | 5 | KQTALVELLK | |
| 6 | 582.320 | 2 | 1162.63 | 1162.62 | 2 | LVNELTEFAK | 22 % |
| 7 | 653.363 | 2 | 1304.71 | 1304.71 | 2 | HLVDEPQNLIK | |
| 8 | 473.907 | 3 | 1418.70 | 1418.69 | 8 | SLHTLFGDELCK | |
| 9 | 480.611 | 3 | 1438.81 | 1438.80 | 4 | RHPEYAVSVLLR | |
| 10 | 493.938 | 3 | 1478.79 | 1478.79 | 3 | LGEYGFQNALIVR | |
| 11 | 756.429 | 2 | 1510.84 | 1510.84 | 6 | VPQVSTPTLVEVSR | |
| 12 | 784.377 | 2 | 1566.74 | 1566.74 | 3 | DAFLGSFLYEYSR | |
| 13 | 547.323 | 3 | 1638.95 | 1638.93 | 9 | KVPQVSTPTLVEVSR | |

Table 2

*Fig. 7B*

| S.No | Observed m/z | Charge | Observed mass (Da) | Theoretical mass (Da) | ppm | Peptide | Sequence coverage |
|---|---|---|---|---|---|---|---|
| 1 | 593.827 | 3 | 1185.640 | 1185.639 | 1 | GPSVFPLAPSSK | |
| 2 | 661.643 | 3 | 1320.672 | 1320.671 | 1 | STSGGTAALGCLVK | |
| 3 | 711.872 | 3 | 2843.458 | 2843.450 | 3 | THTCPPCPAPELLGGPSVFLFPPKPK | |
| 4 | 418.221 | 2 | 834.427 | 834.427 | 0 | DTLMISR | |
| 5 | 713.683 | 3 | 2138.026 | 2138.020 | 3 | TPEVTCVVVDVSHEDPEVK | |
| 6 | 559.941 | 3 | 11376.800 | 11376.795 | 3 | FNWYVDGVEVHNAK | 57 % |
| 7 | 603.343 | 3 | 1807.007 | 1806.999 | 4 | VVSVLTVLHQDWLNGK | |
| 8 | 557.811 | 4 | 2227.214 | 2227.200 | 6 | VVSVLTVLHQDWLNGKEYK | |
| 9 | 419.755 | 2 | 837.496 | 837.496 | 0 | ALPAPIEK | |
| 10 | 643.842 | 2 | 1285.669 | 1285.667 | 2 | EPQVYTLPPSR | |
| 11 | 624.995 | 3 | 1871.964 | 1871.963 | 1 | EPQVYTLPPSRDELTK | |
| 12 | 754.654 | 4 | 3014.585 | 3014.575 | 3 | EPQVYTLPPRDELTIKNQVSLTCLVK | |
| 13 | 581.319 | 2 | 1160.623 | 1160.622 | 0 | NQVSLTCLVK | |
| 14 | 1272.571 | 2 | 2543.128 | 2543.124 | 2 | GFYPSDIAVEWESNGQPENNYK | |
| 15 | 937.466 | 2 | 1872.918 | 1872.915 | 2 | TTPPVLDSDGSFFLYSK | |
| 16 | 625.314 | 3 | 1872.921 | 1872.915 | 3 | TTPPVLDSDGSFFLYSK | |
| 17 | 669.101 | 4 | 2672.374 | 2672.370 | 1 | TTPPVLDSDGSFFLYSKLTVDKSR | |

← Band 1 →

Portion 1 of Table 3 - Ig gamma-1 chain C region; 36596 Da

*Fig. 7C*

| S.No | Observed m/z | Charge | Observed mass (Da) | Theoretical mass (Da) | ppm | Peptide | Sequence coverage |
|---|---|---|---|---|---|---|---|
| 1 | 644.330 | 2 | 1286.646 | 1286.644 | 1 | GPSVFPLAPCSR | 30 % |
| 2 | 712.359 | 2 | 1422.703 | 1422.702 | 1 | STSESTAALGCLVK | |
| 3 | 418.221 | 2 | 834.427 | 834.427 | 1 | DTLMISR | |
| 4 | 598.669 | 3 | 1792.985 | 1792.984 | 8 | VVSVLTVVHQDWLNGK | |
| 5 | 412.751 | 2 | 823.487 | 823.480 | 3 | KGLPAPIEK | |
| 6 | 429.564 | 3 | 1285.670 | 1285.667 | 3 | EPQVYTLPPSREEMTK | |
| 7 | 653.653 | 3 | 1903.936 | 1903.935 | 1 | NQVSLTCLVK | |
| 8 | 581.319 | 2 | 1160.623 | 1160.622 | 0 | NQVSLTCLVK | |
| 9 | 953.452 | 2 | 1904.890 | 1904.887 | 2 | TTPPMLDSDGSFFLYSK | |

*Fig. 7D*

Portion 2 of Table 3 – for Ig gamma-2 chain C region; 36505 Da.

| S.No | Observed m/z | Charge | Observed mass (Da) | Theoretical mass (Da) | ppm | Peptide | Sequence coverage |
|---|---|---|---|---|---|---|---|
| 1 | 488.290 | 3 | 1461.848 | 1461.844 | 3 | VKDLATVYVDVLK | |
| 2 | 618.348 | 2 | 1234.682 | 1234.681 | 1 | DLATVYVDVLK | |
| 3 | 550.962 | 3 | 1234.682 | 1234.681 | 2 | DLATVYVDVLKDSGR | |
| 4 | 603.812 | 4 | 2411.218 | 2411.208 | 4 | DSGRDYVSQFEGSALGKQLNLK | |
| 5 | 700.840 | 2 | 1399.665 | 1399.662 | 2 | DYVSQFEGSALGK | |
| 6 | 737.058 | 3 | 2208.154 | 2208.143 | 5 | QLNLKLLDNWDSVTSTFSK | |
| 7 | 627.994 | 3 | 1880.961 | 1880.963 | 1 | LLDNWDSVTSTFSKLR | |
| 8 | 734.710 | 3 | 2201.109 | 2201.112 | 1 | VLREQLGPVTQEFWDNLEK | 74 % |
| 9 | 966.973 | 2 | 1931.931 | 1931.927 | 2 | EQLGPVTQEFWDNLEK | |
| 10 | 626.815 | 2 | 1251.615 | 1251.614 | 1 | VQPYLDDFQK | |
| 11 | 460.911 | 3 | 1379.710 | 1379.709 | 1 | VQPYLDDFQKK | |
| 12 | 642.295 | 2 | 1282.575 | 1282.565 | 7 | WQEEMELYR | |
| 13 | 431.743 | 4 | 1722.942 | 1722.938 | 3 | QKVEPLRAELQEGAR | |
| 14 | 489.937 | 3 | 1466.789 | 1466.784 | 3 | VEPLRAELQEGAR | |
| 15 | 478.005 | 4 | 1907.992 | 1907.977 | 8 | LHELQEKLSPLGEEMR | |
| 16 | 516.261 | 2 | 1030.508 | 1030.512 | 4 | LSPLGEEMRDR | |
| 17 | 434.889 | 3 | 1301.646 | 1301.640 | 5 | LSPLGEEMRDR | |
| 18 | 470.453 | 5 | 2347.226 | 2347.215 | 5 | AHVDALRTHLAPYSDELRQR | |
| 19 | 434.557 | 3 | 1300.648 | 1300.641 | 5 | THLAPYSDELRQR | |
| 20 | 529.275 | 3 | 1584.803 | 1584.801 | 1 | THLAPYSDELRQR | |
| 21 | 392.978 | 4 | 1567.882 | 1567.879 | 2 | LAARLEALKENGGAR | |
| 22 | 405.879 | 3 | 1214.616 | 1214.614 | 1 | ATEHLSTLSEK | |
| 23 | 338.199 | 3 | 1011.575 | 1011.575 | 4 | AKPALELR | |
| 24 | 410.909 | 3 | 1229.705 | 1229.702 | 2 | QGLLPVLESFK | |
| 25 | 693.864 | 2 | 1385.713 | 1385.708 | 4 | VSFLSALEEYTK | |

Portion3 of Table 3 - Apolipoprotein A-I ; 30759 Da

*Fig. 7E*

| S.No | Observed m/z | Charge | Observed mass (Da) | Theoretical mass (Da) | ppm | Peptide | Sequence coverage |
|---|---|---|---|---|---|---|---|
| 1 | 973.518 | 2 | 1945.022 | 1945.020 | 1 | TVAAPSVFIFPPSDEQLK | |
| 2 | 899.456 | 2 | 1796.898 | 1796.888 | 6 | SGTASVVCLLNNFYPR | |
| 3 | 893.097 | 3 | 2676.270 | 2676.263 | 3 | VQWKVDNALQSGNSQES VTEQDSK | 70 % |
| 4 | 1041.009 | 4 | 4160.006 | 4160.003 | 1 | VQWKVDNALQSGNSQES VTEQDS | |
| 5 | 712.662 | 3 | 2134.963 | 2134.961 | 1 | VDNALQSGNSQESVT EQDSKDSTWSLSSTLTLSK | |
| 6 | 1207.242 | 3 | 3618.705 | 3618.702 | 1 | VDNALQSGNSQESVTE QDSKDSTYSLSSTLTLSK | |
| 7 | 751.883 | 2 | 1501.752 | 1501.751 | 0 | DSTYSLSSTLTLSK | |

Portion 4 of Table 3 - for Ig kappa chain C region; 11773 Da

*Fig. 7F*

MELDRUM'S ACID ACTIVATED FURAN (MAF) MASS SPECTROMETRY COMPATIBLE STAINING AGENT FOR PROTEINS IN POLYACRYLAMIDE GELS

CROSS-REFERENCE TO RELATED DOCUMENTS

The present application claims priority to application No. 202141047710, filed in India on Oct. 20, 2021. All disclosure of the Indian parent application is incorporated in the instant application, at least by reference.

BACKGROUND OF THE INVENTION

1. Field of the Invention

The instant invention is in the technical area of staining agents for proteins in polyacrylamide gels.

2. Description of Related Art

The detection and analysis of proteins is a critical step in a multitude of activities ranging from basic research to enzyme production, forensics analysis and diagnostics. After electrophoretic separation in polyacrylamide gels, the protein profile of a sample is conventionally visualized by staining techniques embodied in Coomassie Brilliant Blue (CBB) and Silver staining methods or via fluorescent stains, such as SYPRO dyes and Deep Purple).

Several studies have explored the protein staining property of naturally occurring dyes in polyacrylamide gels. Presently, CBB staining remains one of the most widely used techniques for protein identification from electrophoretic gels due to its low cost and mass spectrometer compatibility. Recently, cationic dyes like crystal violet which are often used in Gram staining and cell viability assays have also been explored for their potential to stain proteins in SDS-gels.

There remains in the art an unmet need for new and enhanced materials and methods in staining proteins.

BRIEF SUMMARY OF THE INVENTION

In one embodiment of the invention a method for visualizing a macromolecule fragment pattern resulting from gel electrophoresis is provided comprising preparing a polyacrylamide gel in an electrophoresis apparatus, loading a protein sample to a prepared position in the gel, resolving the protein sample by applying an electrical potential across the gel for a period of time, separating molecular fragments of the protein into the fragment pattern in the gel, and treating the polyacrylamide gel with Meldrum's acid Activated Furan (MAF) dissolved in a suitable solvent. The method is characterized in that the MAF stains the molecular fragments in a manner to be discernible by human vision and by conventional analysis techniques.

In one embodiment the MAF is dissolved in dimethyl sulfoxide (DMSO). Also, in obne embodiment one conventional analysis technique is Mass Spectrometry (MS), and the fragment patterns are clearly discernible in MS studies. In one embodiment the electrophoresis apparatus is an apparatus for sodium dodecyl sulphate-polyacrylamide gel electrophoresis (SDS Page). And in one embodiment the MAF prepared Furan-2-carbaldehyde and Meldrum's acid being added sequentially to water, the mixture heated and stirred to accelerate reaction, and the reaction mixture cooled, precipitating MAF as a yellow solid, which is collected by vacuum filtration and dissolved in dichloromethane, then washed and dried in vacuo evaporating the solvent, yielding bright yellow solid MAF. In one embodiment of the method, in the step for resolving the protein sample, in separate runs Bovine serum albumin (BSA), $E.\ coli$ total protein and Plasma proteins were resolved.

In another aspect of the invention a system for visualizing a macromolecule fragment pattern resulting from gel electrophoresis is provided, comprising a polyacrylamide gel in an electrophoresis apparatus, the polyacrylamide gel treated with Meldrum's acid Activated Furan (MAF) dissolved in a suitable solvent as a stain, a protein sample loaded to a prepared position in the gel, and an electrical system resolving the protein sample by applying an electrical potential across the gel for a period of time, separating molecular fragments of the protein into the fragment pattern in the gel. The system is characterized in that the MAF stains the molecular fragments in a manner to be discernible by human vision and by conventional analysis techniques.

In one embodiment of the system the MAF is dissolved in dimethyl sulfoxide (DMSO). Also, in one embodiment the system further comprises mass spectrometry (MS) apparatus, wherein fragment patterns in completed electrophoresis gels are clearly discernible in MS studies. Also, in one embodiment the electrophoresis apparatus is an apparatus for sodium dodecyl sulphate-polyacrylamide gel electrophoresis (SDS Page). In one embodiment the MAF is prepared by Furan-2-carbaldehyde and Meldrum's acid being added sequentially to water, the mixture heated and stirred to accelerate reaction, and the reaction mixture cooled, precipitating MAF as a yellow solid, which is collected by vacuum filtration and dissolved in dichloromethane, then washed and dried in vacuo evaporating the solvent, yielding bright yellow solid MAF. And in one embodiment, in the step for resolving the protein sample, in separate runs Bovine serum albumin (BSA), $E.\ coli$ total protein and Plasma proteins were resolved.

BRIEF DESCRIPTION OF THE SEVERAL VIEWS OF THE DRAWINGS

FIG. 3A shows a set of gels stained at 3 hours.
FIG. 3B shows a set of gels stained at 6 hours.
FIG. 3C shows a set of gels stained at 9 hours.
FIG. 3D shows a set of gels stained at 12 hours.
FIG. 3E shows a set of gels stained with a fixing solution.
FIG. 3F shows a set of gels stained without a fixing solution.

FIG. 5A shows staining sensitivity for CBB R250.
FIG. 5B shows staining sensitivity for CBB G250.
FIG. 5C shows staining sensitivity for CBB R250.
FIG. 7A is Table 1 with a list of peptides identified after MAF staining.
FIG. 7B is Table 2 with a list of peptides identified after CBB staining.
FIG. 7C presents a first of four portions of a table.
FIG. 7D is a second of four portions of the table of FIG. 7C.
FIG. 7E is a third of four portions of the table of FIG. 7C.
FIG. 7F is a fourth of four portions of the table of FIG. 7C.

DETAILED DESCRIPTION OF THE INVENTION 1.0 Introduction

In the present patent application, Meldrum's acid Activated Furan (MAF) is developed, along with procedures for use, as a dye for cost effective and easy colorimetric visualization of proteins. Examples are described, and methods are taught for the use of MAF for this purpose.

MAF is essentially a condensation product of Meldrum's acid with furan-2-carbaldehyde, which is a renewable chemical feedstock. It has been reported that a facile ring opening reaction of MAF with secondary amines afford a new class of compounds called Donor Acceptor Stenhouse Adducts (DASA). Ever since their discovery, DASAs have been widely explored for a wide spectrum of applications including drug delivery, colorimetric sensing, and other applications. The inventors have investigated the reaction of MAF with proteins, which has led to the development of a fast yet accurate colorimetric assay for these ubiquitous biomolecules.

Since the reaction of proteins with MAF has been found to afford colored bioconjugates, the inventors envisaged that this reaction could lead to development of a visible staining technique which could be employed in polyacrylamide gel electrophoresis experiments. In various experiments, samples of Bovine Serum Albumin (BSA) of different concentrations were subjected to SDS-PAGE and the polyacrylamide gels thus obtained were treated with MAF dissolved in dimethyl sulfoxide (DMSO) under various conditions. As the inventors expected, the protein-MAF bioconjugates produced impressive bands with excellent compatibility towards mass spectrometry experiments. Further studies with whole cell proteins from $E.$ $coli$ were carried out to determine the efficacy of the protocol in staining complex protein samples.

2.0 Materials and Methods 2.1 Reagents

Figure 1:
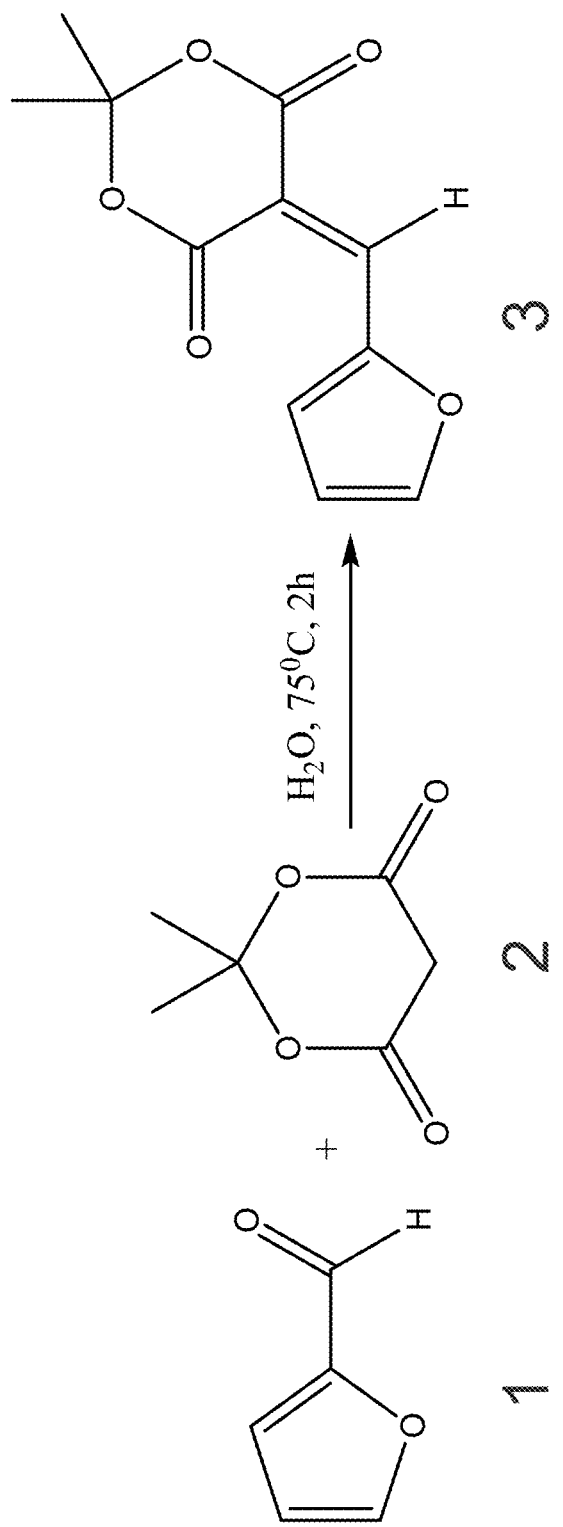
FIG. 1 is an illustration of chemical reaction in producing MAF in an embodiment of the invention.

All chemicals and solvents used in the processes of development in this project were of analytical grade. Furan-2-carbaldehyde, acetic acid (AcOH) and Meldrum's acid were purchased from Spectrochem. Bovine Serum Albumin (BSA), Methanol (MeOH), Dimethyl sulfoxide (DMSO), Bromophenol Blue, dithiothreitol (DTT), iodoacetamide (IAm), trifluoroacetic acid (TFA), Trypsin, Coomassie Brilliant Blue G-250 and R-250 were purchased from Sigma Aldrich. SDS-PAGE gel preparation reagents like Sodium dodecyl sulfate (SDS), tris-(hydroxymethyl)aminomethane (Tris), Acrylamide and bis-acrylamide, Ammonium persulfate (APS) and Tetramethyl ethylenediamine (TEMED) were procured from Bio-Rad. 10-180 kDa protein marker from Origin Diagnostics and Research was used as a protein ladder. Total cellular proteins were extracted from $Escherichia$ $coli$ strain MTCC 40 (Sanitation Biotechnology Lab, Amrita School of Biotechnology, India). 2.2 Synthesis The synthesis and structural characterization of 5-(furan-2-ylmethylene)-2,2-dimethyl-1,3-dioxane-4,6-dione (MAF) was carried out as illustrated in FIG. 1. Furan-2-carbaldehyde, (961 mg, 10 mmol) and Meldrum's acid, and (1.51 g, 10.5 mmol) were added sequentially to 30 mL water. The heterogeneous mixture was heated to 75° C. and stirred for 2 h. On completion of the reaction, the reaction mixture was cooled to room temperature and a precipitated yellow solid was collected by vacuum filtration and dissolved in dichloromethane. The dichloromethane layer was then sequentially washed with 30 ml $H_2O$, 30 ml saturated aqueous $NaHSO_3$, 30 ml saturated aqueous $NaHCO_3$ and 30 ml brine. The organic layer was then separated, dried over $MgSO_4$ and kept in vacuo to evaporate the solvent. About 2.19 g (9.86 mmol, 98.5% yield) of the compound MAF was obtained as a bright yellow solid.

2.3 Protein Visualization in SDS-PAGE Gel 2.3.1 Sds-Page

Bovine serum albumin (BSA), $E.$ $coli$ total protein and Plasma proteins were resolved on polyacrylamide gel using a Bio-Rad Miniprotean® system. Stacking and resolving gels were of concentrations 5% and 10% respectively with a 29:1 acrylamide: bisacrylamide ratio. Gel preparation contained 30% (w/v) acrylamide, 10% (w/v) SDS, 10% (w/v) APS and TEMED with resolving gel prepared at a pH of 8.8 using 1.5M Tris and stacking gel at a more acidic pH of 6.8 using 1 M Tris. An electrode buffer composed of 25 mM Tris, 192 mM glycine and 0.1% (w/v) SDS was used for the electrophoresis of the gel at 150 V for less than 2 h. The protein samples were prepared in 4X loading dye (after adding mercaptoethanol) and heated in a water bath at 95° C. for 3-5 mins.

2.3.2 MAF Staining

The BSA bands obtained in the gels from the SDS-PAGE experiments were stained using MAF concentrations varying from 25-100 mg per mL DMSO. The gels were treated with a fixing solution (AcOH:MeOH:$H_2O$, 10:45:45 v/v) for 30 minutes followed by staining with MAF reagent. After incubating at different time intervals, the gels were washed and de-stained using distilled water for 2-3 hours. Similarly, $E.$ $coli$ total protein and plasma proteins were also subjected to MAF staining at 100 mg/ml for 12 hours. The protein bands obtained were analyzed using a gel doc system from Bio-Rad (ChemiDoc™ XRS+Imaging System).

2.3.3 CBB Staining

Proteins resolved by SDS-PAGE were stained with solutions containing 0.25% (w/v) CBB R-250 (or CBB G-250) following the classical Neuhoff method [2]. After overnight incubation, the gels were destained by consecutive washes at every 2 hours with a solution containing 40% (v/v) methanol and 10% (v/v) glacial acetic acid.

2.4 Mass Spectrometric Analysis 2.4.1 In-Gel Digestion

After de-staining the gel bands were cut into smaller pieces and subjected to reduction using 10 mM DTT followed by incubation at 56° C. for 45 minutes. Later, the gel pieces were allowed to cool at room temperature and the leftover DTT was aspirated. Subsequently, the gel pieces were subjected to alkylation using 55 mM IAm and incubated in the dark for 30 minutes. After dehydrating the gel pieces using 100% acetonitrile, they were rehydrated with 50 mM ammonium bicarbonate buffer containing 13 ng/μL trypsin and incubated at 37° C. overnight. The digested peptides were then extracted by adding 50% acetonitrile containing 0.1% TFA and the resulting supernatant was dried completely using a vacuum concentrator Reference source not found.

2.4.2 Q-TOF LC-MS/MS Analysis

For MS analysis, a mass spectrometer (Agilent 6540 Q-TOF LC/MS) equipped with a chip cube source and coupled to a 1260 cap/nano HPLC system was used. Water with 0.1% formic acid was used as the mobile phase A and 90% ACN with 0.1% formic acid as mobile phase B.

The capillary pump flow rate (for sample loading) and nano pump flow rate (for peptide separation) were maintained at 3 μL/min and 0.3 μL/min, respectively. The trypsin-digested peptide samples were infused into the mass spectrometer through a chip having built-in enrichment and analytical reversed-phase columns (Agilent ZORBAX SB-C18, 75 μm ×150 mm, 5 μm) fitted with a nanospray emitter. Peptide separation was achieved using the following time program: 5% B for 2 min, 5-45% B for 33 min, 45-90% for 5 min. The parameters used for MS data acquisition were as follows: MS-250 to 3000 m/z; MS/MS-50 to 3000 m/z; capillary voltage-2000 V; fragmentor voltage-150 V; source temperature-325° C.; nebulizer pressure-15 psi; dry gas flow rate-4 L/min; preferred charge states-2, 3 and >3; MS scan speed-4 spectra/s; MS/MS scan speed-3 spectra/s; maximum number of precursors-5; active exclusion-enabled by excluding after 2 spectra and releasing after 0.25 minutes. Agilent Mass Hunter software was used for MS control and data acquisition.

2.4.3 Identification of Proteins

The acquired MS raw data was converted to .mgf file format using Agilent Mass Hunter software followed by Mascot (version 2.5.1, Matrix Science, UK) search against Swiss-Prot database. 10 ppm and 0.5 Da were respectively set as peptide mass tolerance and fragment mass tolerance. Trypsin was chosen as the protease with a maximum of two missed cleavages. Carbamidomethylation of cysteine was selected as the fixed modification and oxidation of methionine and deamidation of asparagine and glutamine were selected as the variable modifications. For false discovery rate calculation, target-decoy database searches were performed.

3.0 Results and Discussion

Bioconjugation of proteins with Meldrum's acid-activated Furan was found to be a versatile method to stain these ubiquitous biomolecules in polyacrylamide gels. The technique is based on a facile nucleophilic attack at the 5-position of the furan ring of MAF by the amine functionalities on proteins to form a deep brown color, which makes it visible in the gel matrix, thereby providing information regarding the quantity and molecular weight of the proteins, separation efficiency within the electrophoretic system, and so on. The detailed chemical mechanism of the protein bioconjugation is currently under investigation. In a typical staining procedure, 10% SDS-PAGE gels were used to separate the proteins which were later fixed on the gel by incubation in fixing solution (AcOH: MeOH: $H_2O$, 10:45:45 v/v) for 30 minutes followed by treatment with MAF reagent (25-100 mg/ml of DMSO). De-staining of the gel background was done with distilled water. Further analysis including the relative densitometric calculations proves that the MAF staining is an efficient method to visualize proteins in polyacrylamide gels, with staining intensities comparable to that of Coomassie Brilliant Blue R-250.

3.1 MAF Staining of Proteins in Polyacrylamide Gels: Optimization of Parameters

The reactions of Meldrum's acid Activated Furans with secondary amines as well as peptides to enable colored products were extended to proteins for exploiting the potential of this reaction to visualize proteins in polyacrylamide gels. It was envisaged that this facile reaction of MAF with proteins could be exploited in the development of a new staining dye for proteins. As expected, it was observed that the protein bands in the gel were stained deep brown, indicating the formation of MAF-protein bioconjugates and having staining intensity comparable to that of CBB. The optimum MAF concentration that can effectively stain protein in polyacrylamide gel was determined as follows: Four sets of the protein, BSA at different concentrations (with a final amount of 22, 11, 5.6 and 0.5 μg BSA loaded to the wells in each set) were run through 1-D SDS-PAGE. The gels were stained with MAF at varying concentrations (25-100 mg/ml), followed by fixation for 30 minutes.

FIGS. 2A through 2D illustrate BSA samples of from 0.5 to 22 μg run on polyacrylamide gel and stained using 25, 50, 75 and 100 mg/ml MAF respectively.

Figure 2A:
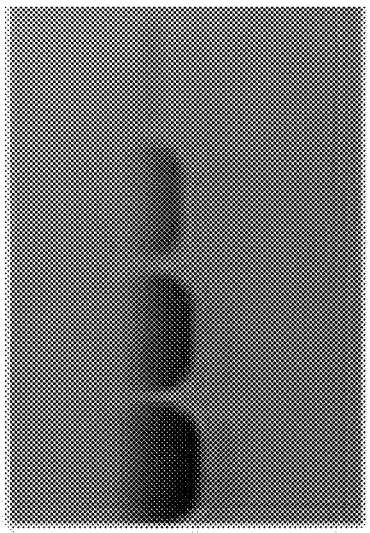
FIG. 2A shows a set of four samples of BSA run on polyacrylamide gel and stained using 25 mg/ml MAF.
Figure 2B:
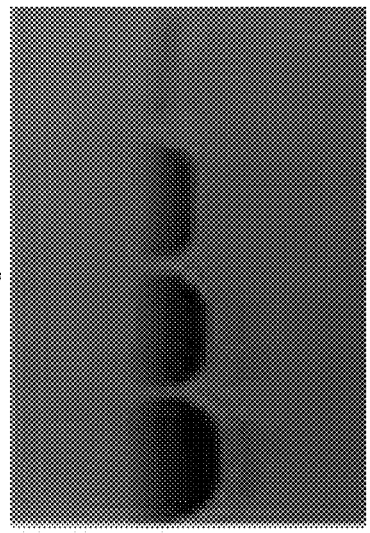
FIG. 2B shows a set of four samples of BSA run on polyacrylamide gel and stained using 50 mg/ml MAF.
Figure 2C:
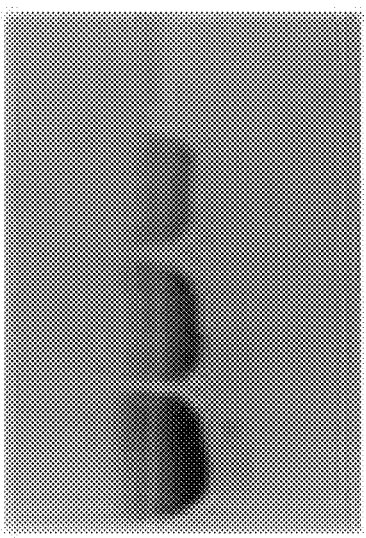
FIG. 2C shows a set of four samples of BSA run on polyacrylamide gel and stained using 75 mg/ml MAF.
Figure 2D:
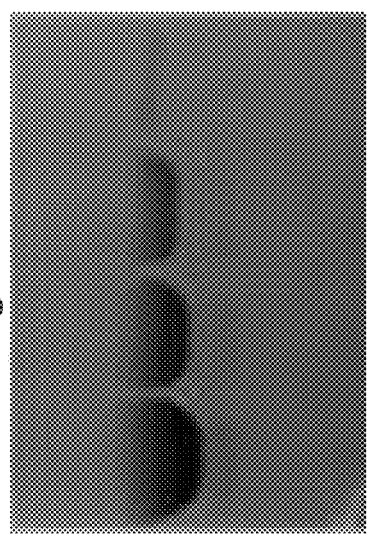
FIG. 2D shows a set of four samples of BSA run on polyacrylamide gel and stained using 100 mg/ml MAF.
Figure 2E:
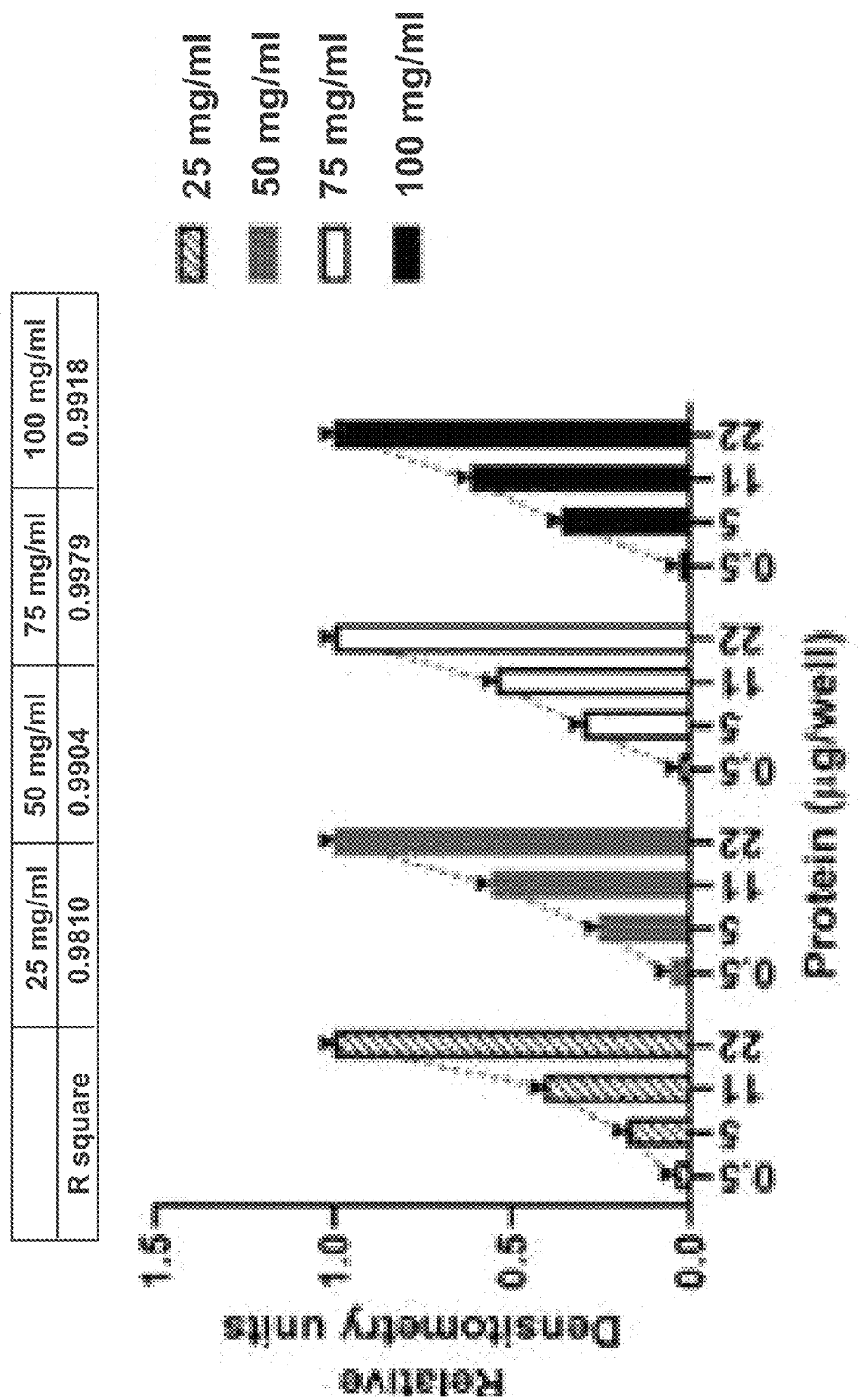
FIG. 2E shows relative densitometry values of 0.5-22 µg BSA, showing relative change in band density.

FIG. 2E illustrates relative densitometry values of 0.5-22 μg BSA samples calculated taking 22 μg band as unit value. The relative change in band density at different MAF stain concentrations are represented in histogram.

Figure 2F:
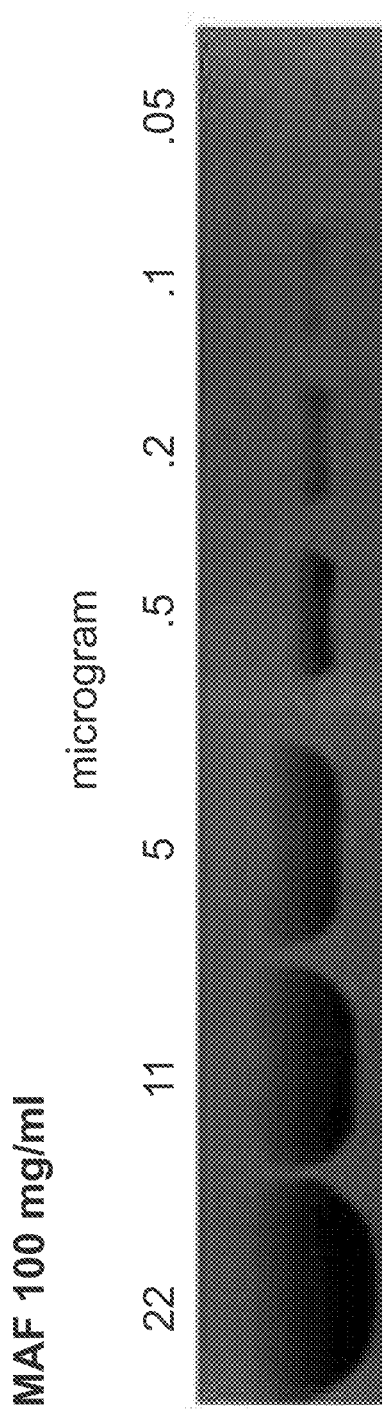
FIG. 2F shows seven samples of BSA run on polyacrylamide gel and stained using 100 mg/ml MAF.

FIG. 2F illustrates 0.05, 0.1, 0.2, 0.5, 5, 11, 22 μg samples of BSA run on polyacrylamide gel and stained using 100 mg/ml MAF.

The bands obtained after destaining, represented in FIGS. 2A through 2D, indicate that MAF ranging from 25-100 mg/ml may well be employed as a staining agent for proteins in gel electrophoresis. Though all the four concentrations of MAF showed linear response, staining with 50-100 mg/ml MAF resulted in more intense bands with better correlation value ($r^2$=0.99) in gel doc analysis (FIG. 2E). Thus 75 mg/ml and 100 mg/ml of MAF was used to stain gels that contain high (≥1000 ng) and low (≤1000 ng) amounts of protein respectively in further studies. It was observed that MAF staining demonstrated linear response to varying concentrations of BSA with a concentration dependent increase in the densitometry values. Staining was done over a range of BSA from 0.05 to 22 μg with 100 mg/ml MAF. (FIG. 2F).

FIG. 3A shows a set of two gels with 5 and 0.5 μg BSA stained at 3 hours. FIG. 3B shows a set of two gels with 5 and 0.5 μg BSA stained at 6 hours. FIG. 3C shows a set of two gels with 5 and 0.5 μg BSA stained at 9 hours. FIG. 3D shows a set of two gels with 5 and 0.5 μg BSA stained at 12 hours. From 3 h to 12 h the band density of 5 μg protein is seen to increase by a factor of 2.6 and that of 0.5 μg increased by a factor of 2.8.

FIGS. 3E and 3F show effect staining with and without a fixing solution. The experiments were performed with samples of 22 and 11 μg BSA. From the triplicates, a CV of 4.9% was obtained.

In order to optimize the incubation period, gels with 5 and 0.5 μg BSA after electrophoresis were kept in 75 mg/ml MAF staining solution for varying time points (3h, 6h, 9h and overnight incubation). Though the densitometry ratio between the two bands obtained after de-staining remained the same, the band density increased with time. Bands obtained after overnight staining were almost three times denser than at 3 hours as seen in FIGS. 3A-3D. Therefore, further experiments were carried out with an overnight treatment period of 12-15 hours.

To evaluate the extent of interference of SDS on MAF-protein interaction which could lead to protein loss, the staining was performed without using the fixing solution. To this end, 22 and 11 µg of protein were resolved in 1D SDS-PAGE in duplicates. Later, one half of the gel was subjected to fixation prior to MAF staining for 30 minutes and the other half without subjecting to fixation procedure. The representative images obtained are shown in FIGS. 3E and 3F. The band intensity in both staining conditions is analysed densitometrically and has a mean ratio of 1.003 (with fixing solution: without fixing solution). The experiment done in triplicate gave a cumulative variance of 4.9% indicating the reproducibility of the finding. The studies using MAF as a reagent for protein quantitation revealed that the assay has minimal interference of SDS on MAF-protein interaction, whereas SDS to interfere with the binding of CBB to protein in polyacrylamide gels.

3.2 The MAF Staining: Sensitivity Studies

Figure 4A:
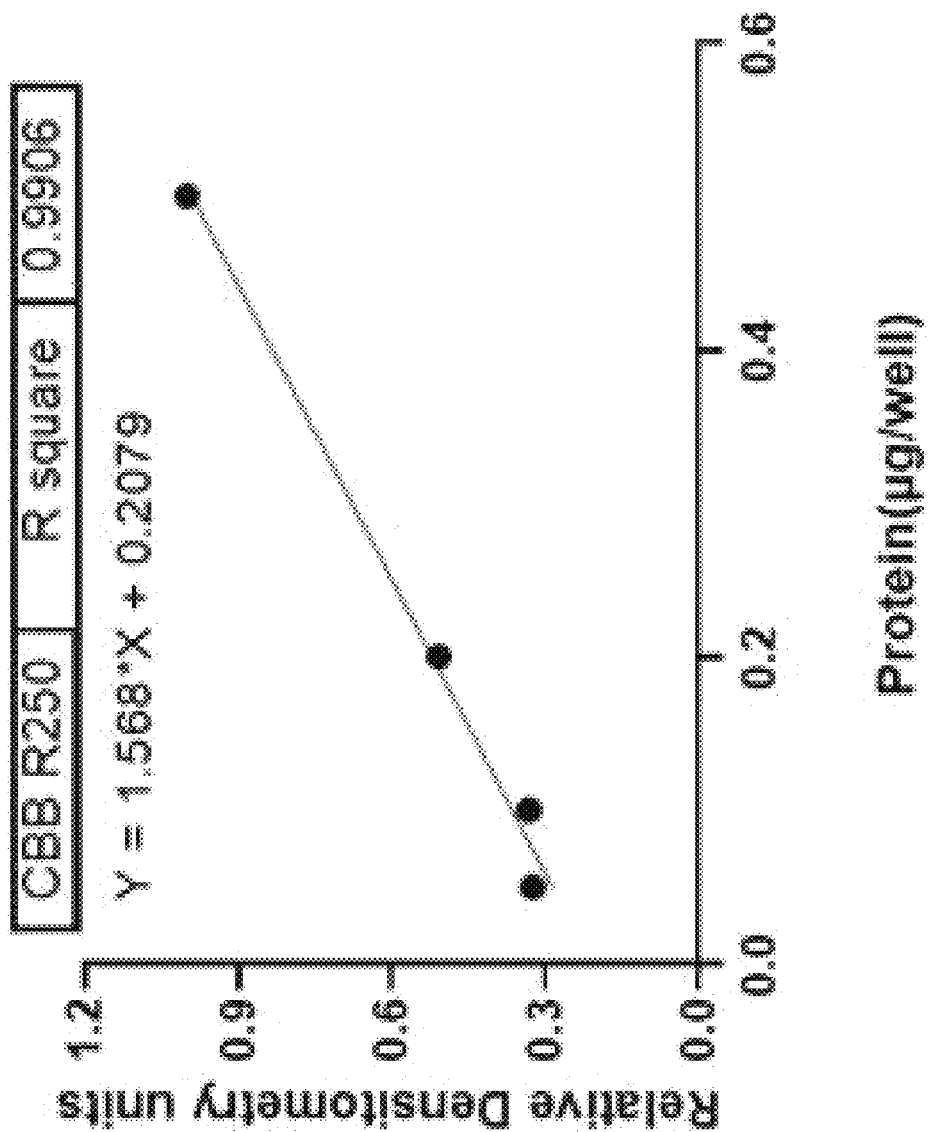
FIG. 4A shows density in relative densitometry units for varying protein in µg for CBB R250.
Figure 4B:
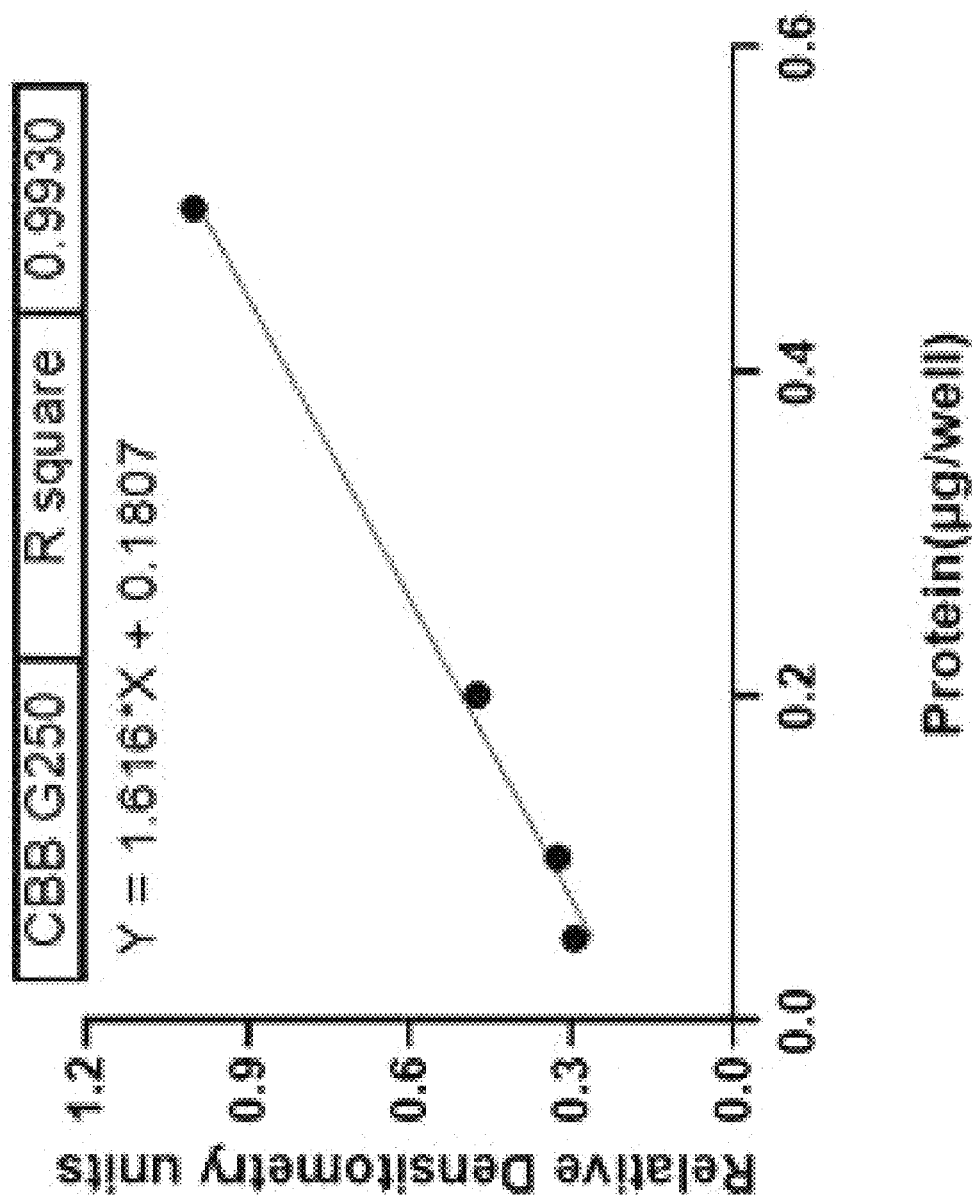
FIG. 4B shows the relationship for CBB G250.
Figure 4C:
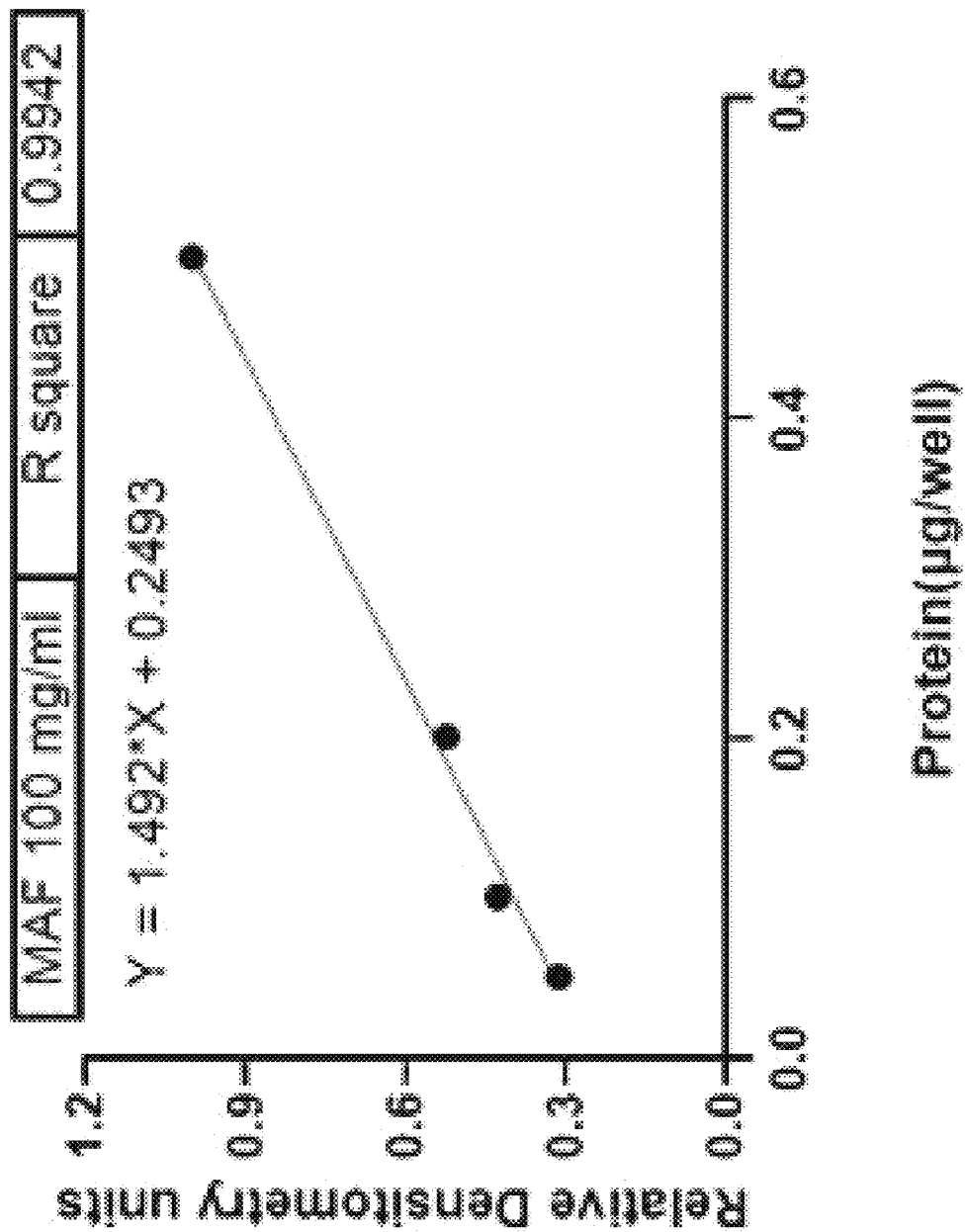
FIG. 4C shows the relationship for MAF 100 mg/ml.

Since initial studies indicate that MAF reagent-based staining is a promising method for protein quantification in polyacrylamide gel, further experiments were carried out to estimate the detection limit of the staining procedure. To this end, sensitivity of MAF based protein staining technique was compared with the two most widely used commercial PAGE staining dyes, CBB R-250 and CBB G-250. FIG. 4A shows density in relative densitometry unis for varying protein in µg for CBB R250. FIG. 4B shows the relationship for CBB G250. FIG. 4C is for MAF 100 mg/ml.

Sensitivity was compared by analysing the slope of the calibration curves. All three methods showed comparable sensitivity with CBB techniques R250 and G250 having slope of 1.57 and 1.62 Relative Densitometry units/protein concentration respectively, while MAF stain showed a slope of 1.5 Relative Densitometry units/protein concentration.

In order to note the detection limit (lowest amount of protein that can be estimated from a MAF stained gel), a MAF concentration of 100 mg/ml was used. Three sets of gels were loaded with 500-50 ng BSA and were stained in CBB R-250, CBB G-250 and MAF 100 mg/ml respectively. FIGS. 5A-5C show the relative densitometry values for all protein bands, assuming unit value for the band obtained with CBB R250. All the three staining methods were sensitive up to 50 ng BSA loaded in the gel, where comparable relative densitometry values were obtained of 1 and 1.1 for CBB R250 and MAF respectively. For individual staining methods it can also be observed that the band intensity increases with protein concentrations and exhibited a linear response when analyzed by densitometric studies. This observation was found to be in good agreement with the concentration optimization studies described above in section 3.1. Limit of detection (LOD) values were calculated for the three gels using the equation, LOD=$3S_a$/b, where $S_a$ is the standard deviation of y-intercepts of the regression line and b is the slope of the calibration curve Reference source not found., Reference source not found. LOD values of $6.2\times10^{-2}$ µg and $5.4\times10^{-2}$ µg were obtained for CBB R-250 and CBB G-250 respectively whereas gels stained with MAF reported the lowest LOD value of $4.9\times10^{-2}$ µg. The results suggest that MAF may effectively stain as low as 50 ng protein in SDS-PAGE gels.

Currently, identification of proteins from various in vitro and in vivo environments such as whole cell lysate, plasma and serum remains a challenge, as this demands a better separation and identification technique with better resolution. This also has to be compatible with further downstream identification using MS. To analyze the efficacy of MAF in staining complex protein mixtures, the whole protein from E. coli cell lysate was isolated by TRIzol method, separated through SDS-PAGE at different dilutions and then stained using the MAF protocol (100 mg/ml MAF). As expected, the MAF reagent was found to be efficient in staining the proteins in a crude sample containing a mixture of proteins.

Figures 5D, 5E:
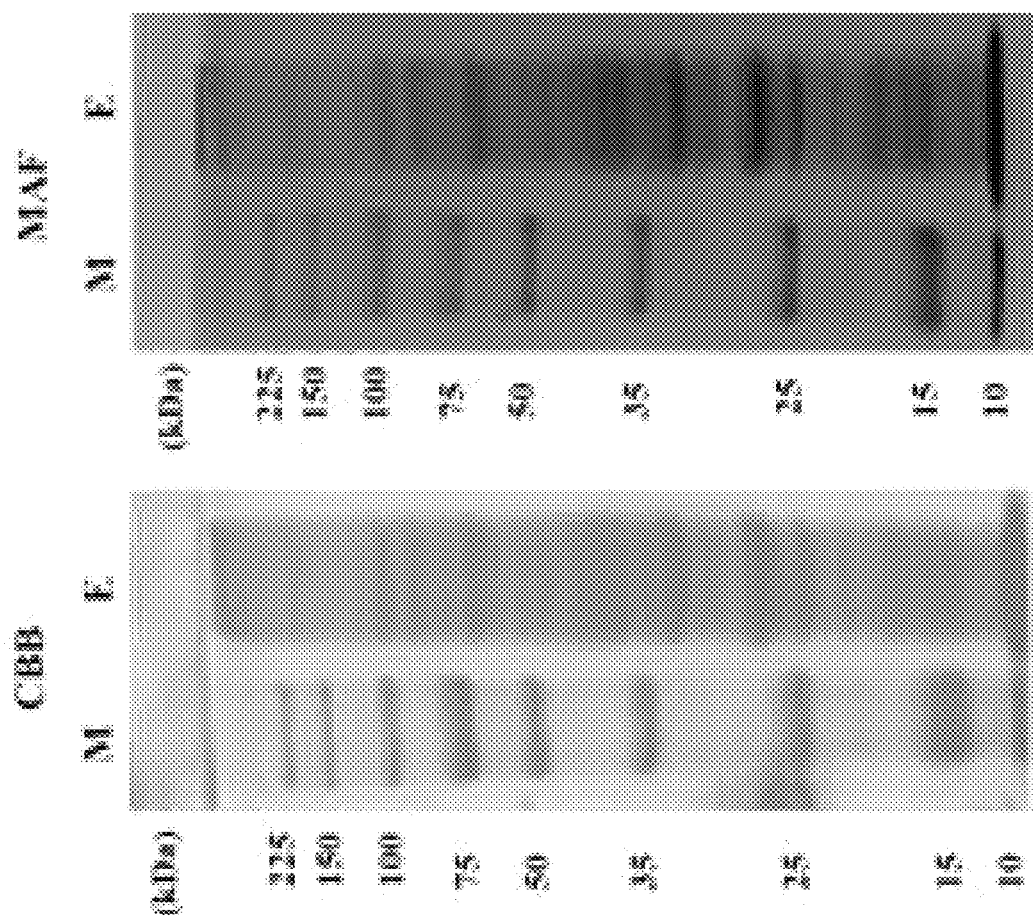
FIG. 5D shows CBB staining.
FIG. 5E shows MAF staining for comparison to FIG. 5D.

FIG. 5A shows staining sensitivity for CBB R250 varying protein from 0.5 to 0.05 µg. FIG. 5B shows staining sensitivity for CBB G250 varying protein from 0.5 to 0.05 µg. FIG. 5C shows staining sensitivity for CBB R250 varying protein from 0.5 to 0.05 µg. FIG. 5D represents the gel images of whole cell lysate E (with 26 µg protein) stained with MAF, and FIG. 5E the gel images for CBB 250. The results obtained indicate that the bands derived after MAF staining showed comparable results with that of CBB R-250 stain in identifying protein components present in E. coli extract.

3.3 Compatibility Studies of MAF Staining Protocol in Mass Spectrometric Analysis LC-MS/MS and subsequent database analysis of CBB and MAF stained protein bands were confirmed to be representing bovine serum albumin with comparable sequence coverage. It was observed that CBB stained gels yielded approximately 22% coverage while MAF afforded 15% coverage. The peptides identified from MAF stained gels are listed in Table 1 and Table 2.

Figure 6A:
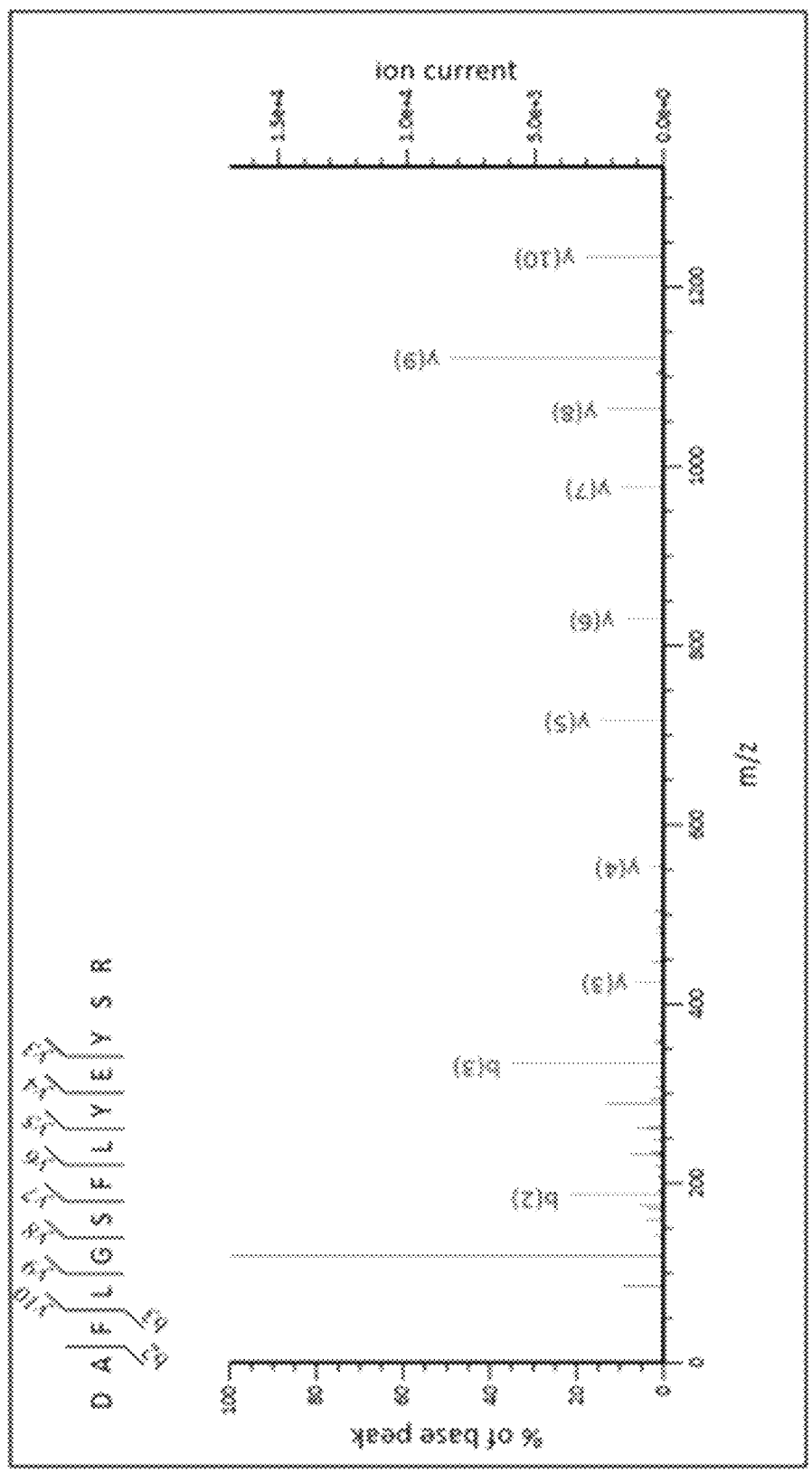
FIG. 6A shows MS/MS data of a representative peptide.
Figure 6B:
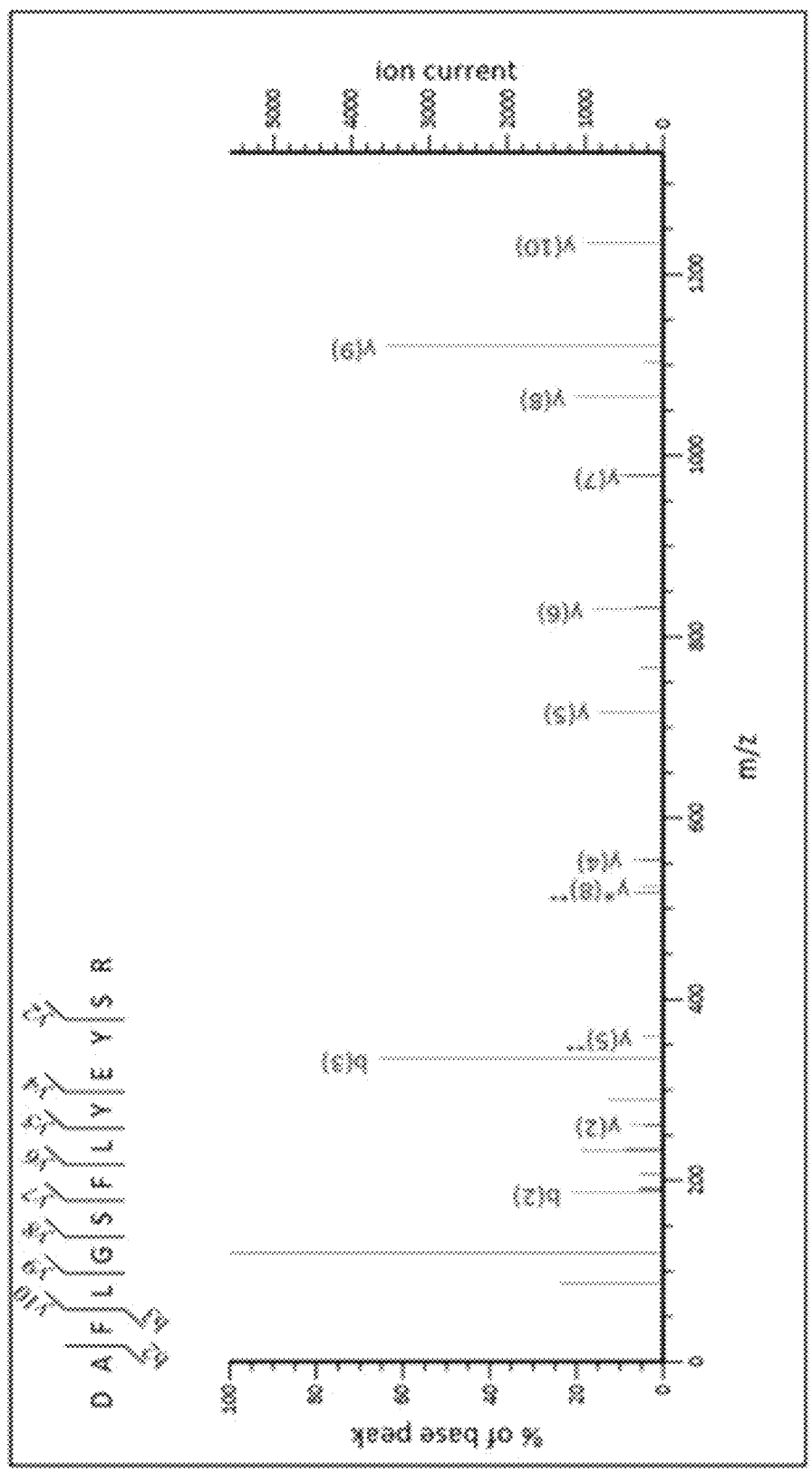
FIG. 6B shows MS/MS data of another representative peptide
Figure 6C:
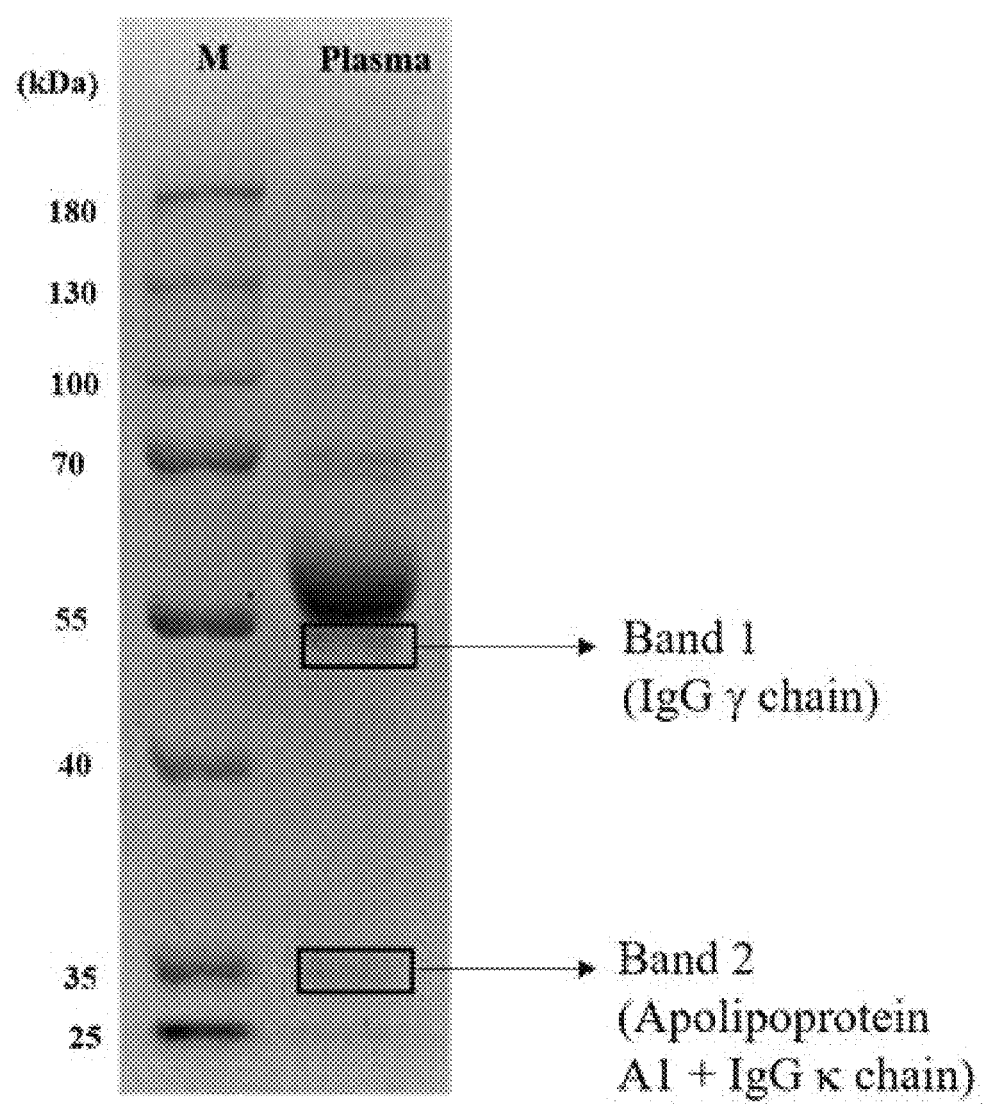
FIG. 6C shows two chains with impressive sequence coverage.

FIGS. 6A and 6B respectively show MS/MS data of a representative peptide, DAFLGSFLYEYSR generated from the CBB and MAF stained gels. As evident from the spectra there is significant similarity in the MS/MS fragmentation patterns. Compatibility of MAF staining protocol to mass spectrometry was further confirmed by analyzing the plasma proteins. The results indicate that the identified proteins such as immunoglobulin gamma-1 and 2 chains (57% and 30%), apolipoprotein (74%) and immunoglobulin kappa chain (70%) (Table 3, FIG. 6C) have impressive sequence coverage. All these results suggest that MAF staining of proteins in SDS-PAGE gels is compatible with mass spectrometric analysis.

FIG. 7A presents Table 1, which lists peptides identified from BSA after MAF staining and subsequent proteomic analysis.

FIG. 7B presents Table 2, which is a list of peptides identified from BSA after CBB staining and subsequent proteomic analysis.

FIG. 7C presents a first of four portions of Table 3, which is a list of proteins identified from plasma through MAF, for Ig gamma-1 chain C region; 36596 Da.

FIG. 7D is a second of four portions of Table 3, which is a list of proteins identified from plasma through MAF, for Ig gamma-2 chain C region: 36505 Da.

FIG. 7E is a third of four portions of Table 3, which is a list of proteins identified from plasma through MAF, for Apolipoprotein A-I; 30759 Da.

FIG. 7F is a fourth of four portions of Table 3, which is a list of proteins identified from plasma through MAF, for Ig kappa chain C region: 11773 Da.

4.0 Conclusion

Meldrum's acid-activated Furan (MAF) was employed as a reagent to stain proteins resolved by SDS-PAGE. Proteins, ubiquitous biomolecules, were found to react with MAF in DMSO to yield colored bioconjugates in a facile reaction which takes place at room temperature. It was observed that MAF reagent afforded impressive protein bands with intensities comparable to that of CBB stains. The experiments also confirmed that MAF can stain up to 50 ng protein in the gels, which is comparable with the sensitivity limit of the most widely used CBB R-250 dye.

To assess resolving capacity of the reagent, *E. coli* cell lysate was stained with MAF and compared with gel stained with CBB 250. It was observed that all bands identified in CBB protocol were also well resolved in the MAF stained gels.

Finally, mass spectrometric analysis of protein gels stained using MAF protocol resulted in identical fragmentation patterns as obtained using CBB protocol with a sequence coverage of 15% for BSA. In addition, the mass spectrometric studies extended to plasma proteins resulted in considerable sequence coverage for different proteins including immunoglobulins and apolipoproteins which confirms the compatibility of the MAF staining protocol with MS analyses.

The skilled person will understand that procedures established in examples above and embodiments described are exemplary, and that variations may well fall within the scope of the invention. The scope of the invention is limited only by the scope of the claims.

We claim:

1. A method for visualizing a macromolecule fragment pattern resulting from gel electrophoresis, comprising:
   preparing a polyacrylamide gel in an electrophoresis apparatus;
   loading a protein sample to a prepared position in the gel;
   resolving the protein sample by applying an electrical potential across the gel for a period of time, separating molecular fragments of the protein into the fragment pattern in the gel; and
   treating the polyacrylamide gel with Meldrum's acid Activated Furan (MAF) dissolved in a suitable solvent;
   characterized in that the MAF stains the molecular fragments in a manner to be discernible by human vision and by conventional analysis techniques.

2. The method of claim 1 wherein the MAF is dissolved in dimethyl sulfoxide (DMSO).

3. The method of claim 1 wherein one conventional analysis technique is Mass Spectrometry (MS), and the fragment patterns are clearly discernible in MS studies.

4. The method of claim 1 wherein the electrophoresis apparatus is an apparatus for sodium dodecyl sulphate-polyacrylamide gel electrophoresis (SDS Page).

5. The method of claim 1 wherein the MAF is prepared by Furan-2-carbaldehyde and Meldrum's acid being added sequentially to water, the mixture heated and stirred to accelerate reaction, and the reaction mixture cooled, precipitating MAF as a yellow solid, which is collected by vacuum filtration and dissolved in dichloromethane, then washed and dried in vacuo evaporating the solvent, yielding bright yellow solid MAF.

6. The method of claim 1 wherein in the step for resolving the protein sample, in separate runs Bovine serum albumin (BSA), *E. coli* total protein and Plasma proteins were resolved.

7. A system for visualizing a macromolecule fragment pattern resulting from gel electrophoresis, comprising:
   a polyacrylamide gel in an electrophoresis apparatus, the polyacrylamide gel treated with Meldrum's acid Activated Furan (MAF) dissolved in a suitable solvent as a stain;
   a protein sample loaded to a prepared position in the gel; and
   an electrical system resolving the protein sample by applying an electrical potential across the gel for a period of time, separating molecular fragments of the protein into the fragment pattern in the gel;
   characterized in that the MAF stains the molecular fragments in a manner to be discernible by human vision and by conventional analysis techniques.

8. The system of claim 7 wherein the MAF is dissolved in dimethyl sulfoxide (DMSO).

9. The system of claim 7 further comprising mass spectrometry (MS) apparatus, wherein fragment patterns in completed electrophoresis gels are clearly discernible in MS studies.

10. The system of claim 7 wherein the electrophoresis apparatus is an apparatus for sodium dodecyl sulphate-polyacrylamide gel electrophoresis (SDS Page).

11. The system of claim 7 wherein the MAF is prepared by Furan-2-carbaldehyde and Meldrum's acid being added sequentially to water, the mixture heated and stirred to accelerate reaction, and the reaction mixture cooled, precipitating MAF as a yellow solid, which is collected by vacuum filtration and dissolved in dichloromethane, then washed and dried in vacuo evaporating the solvent, yielding bright yellow solid MAF.

12. The system of claim 7 wherein in the step for resolving the protein sample, in separate runs Bovine serum albumin (BSA), *E. coli* total protein and Plasma proteins were resolved.

* * * * *